United States Patent
Dickson

(10) Patent No.: US 9,301,552 B2
(45) Date of Patent: Apr. 5, 2016

(54) ANTI-SLIP STOCKING SOLE

(75) Inventor: Dianne Dickson, Balgowlah (AU)

(73) Assignee: DICKSON & DICKSON HEALTHCARE LIMITED, New South Wales (AU)

( * ) Notice: Subject to any disclaimer, the term of this patent is extended or adjusted under 35 U.S.C. 154(b) by 55 days.

(21) Appl. No.: 13/882,794

(22) PCT Filed: Oct. 25, 2011

(86) PCT No.: PCT/AU2011/001365
§ 371 (c)(1),
(2), (4) Date: Dec. 11, 2013

(87) PCT Pub. No.: WO2012/058708
PCT Pub. Date: May 10, 2012

(65) Prior Publication Data
US 2014/0128785 A1    May 8, 2014

(30) Foreign Application Priority Data

Nov. 1, 2010    (AU) ................................ 2010238563

(51) Int. Cl.
| A41B 11/00 | (2006.01) |
| A61F 13/08 | (2006.01) |
| A61H 1/00 | (2006.01) |

(52) U.S. Cl.
CPC ............... *A41B 11/008* (2013.01); *A61F 13/08* (2013.01); *A61H 1/008* (2013.01)

(58) Field of Classification Search
CPC ...... A43B 17/00; A43B 17/003; A43B 17/14; A43B 17/026; A43B 7/14; A43B 13/00; A43B 13/22; A43B 3/128; A43B 3/246; A41B 11/02; A41B 11/003; A41B 11/00; A41B 11/002; A41B 11/008; A41B 11/007; A41B 2400/80; A61F 13/08; A61F 13/06; A61F 13/064; A61F 13/066; A61F 13/067; A61F 5/0111; A41D 13/06; A41D 17/02; D04B 1/26
USPC .............. 2/239, 241, 242; 602/62, 63, 75–77; 36/103, 25 R, 28, 30 R, 30 A, 32 R, 36/59 A–59 D, 59 R
See application file for complete search history.

(56) References Cited

U.S. PATENT DOCUMENTS

| 4,021,860 | A | 5/1977 | Swallow et al. |
| 4,027,667 | A * | 6/1977 | Swallow et al. ................ 602/63 |
| 4,069,515 | A * | 1/1978 | Swallow et al. .................. 2/239 |

(Continued)

FOREIGN PATENT DOCUMENTS

| JP | 52-126332 A | 10/1977 |
| JP | 3058783 U | 6/1999 |

(Continued)

OTHER PUBLICATIONS

Japanese Notice of Reasons for Rejection for JP2013-536955 dated Aug. 31, 2015, with English Translation.

*Primary Examiner* — Andrew W Collins
(74) *Attorney, Agent, or Firm* — Browdy and Neimark, PLLC

(57) ABSTRACT

A compression stocking is described with anti-slip means at the bottom surface of the stocking sole. The anti-slip means comprises one or more elongate grip members having a wave shape. The sole comprises a fabric tread and at least a portion of the elongate grip members overlies the tread.

13 Claims, 2 Drawing Sheets

(56) References Cited

U.S. PATENT DOCUMENTS

| | | | |
|---|---|---|---|
| 4,149,274 A * | 4/1979 | Garrou et al. | 2/239 |
| 5,412,957 A * | 5/1995 | Bradberry et al. | 66/178 A |
| 5,708,985 A * | 1/1998 | Ogden | A41B 11/02 2/239 |
| 6,378,139 B1 | 4/2002 | Mazzaglia | |
| 7,346,935 B1 * | 3/2008 | Patterson | 2/239 |
| 8,220,077 B1 * | 7/2012 | Ott et al. | 2/239 |
| 2005/0144703 A1 * | 7/2005 | Hilbert | 2/239 |
| 2006/0195972 A1 * | 9/2006 | Alley | 2/239 |
| 2007/0028365 A1 * | 2/2007 | Williams | 2/239 |
| 2009/0126082 A1 * | 5/2009 | Janes | 2/239 |
| 2010/0088804 A1 * | 4/2010 | Crosby | 2/239 |
| 2012/0090077 A1 * | 4/2012 | Brown | 2/239 |

FOREIGN PATENT DOCUMENTS

| | | |
|---|---|---|
| JP | 2000-73203 A | 3/2000 |
| JP | 3134462 U | 8/2007 |
| JP | 2007-239151 A | 9/2007 |
| WO | 2009101642 A1 | 8/2009 |

* cited by examiner

ANTI-SLIP STOCKING SOLE

CROSS-REFERENCE TO RELATED APPLICATION

The present application claims priority from Australian Provisional Patent Application No 2010238563 filed on 1 Nov. 2010, the content of which is incorporated herein by reference.

FIELD

The present invention relates to stockings, particularly compression stockings.

BACKGROUND

Compression stockings, also known as therapeutic or anti-embolism stockings, apply a compressive pressure to a wearer's leg. The stockings are usually worn by a person whose movement is limited, e.g., after an operation or during a long haul airplane flight. A reduction in movement can cause a decrease in the velocity of blood flow in the person's legs, increasing the risk of thrombosis or embolism. By applying pressure to the leg, the velocity of blood flow can be increased, minimising these risks.

Compression stockings are often worn without shoes, making the wearer particularly prone to slipping. A hospital patient may be more prone to slipping as they may be relatively weak or disabled, and hospital floors can be highly polished. Currently, many hospitals provide patients with non slip overboots to prevent slipping. However, this increases hospital costs and patients may not necessarily wear the overboots.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention relates to a compression stocking comprising one or more anti-slip features. The configuration of the compression stocking may prevent the wearer falling, and it may therefore be considered an anti fall non slip stocking.

According to a first aspect, the present invention provides a compression stocking comprising:

a foot portion for covering at least portion of a wearer's foot, the foot portion including a toe region and a heel region and a sole extending between the toe region and heel region, the sole having a bottom surface for contacting a floor; and anti-slip means provided at the bottom surface of the sole, the anti-slip means comprising one or more elongate grip members having a wave shape.

By providing one or more elongate grip members having a wave shape, the elongate grip members may stretch in conformity with the sole during use. It is desirable that all or part of the anti-slip means stretches in conformity with the sole, so that it does not adversely affect the stocking's stretch characteristics, ensuring that appropriate pressure to the wearer's leg or foot can be applied. By stretching in conformity with the sole, the anti-slip means may avoid damage, e.g. avoid tearing, as the sole is stretched.

As the grip members stretch, the wave shape of the grip members may resemble more closely a straight line shape. In other words, the amplitude of the wave shape of each grip member may decrease as the length of the grip member increases. This ability of the grip members to stretch by straightening out may at least partially enable the grip members to stretch in conformity with stretching of the sole. Additionally, the grip members may be formed of elastic, stretchable material.

In addition to the improved stretch characteristics, by providing grip members with a wave shape, the grip members can have a relatively large amount of both laterally facing surface regions and longitudinally facing surface regions, providing the stocking sole with improved anti-slip properties in multiple directions.

The wave shape may be a zigzag shape, a sinusoidal shape or other wave shape. Oscillations making up the wave shape may be uniform or non-uniform. When a plurality of the grip members are provided, the wave shape of each grip member may be the same or different. Different wave shapes may have different wavelengths (peak to peak distances), different amplitudes (peak to trough distances), and/or different patterns of oscillation. Grip members having different wave shapes may be employed depending on the respective locations of the grip members on the bottom surface of the sole, and the stretch characteristics, or desired stretch characteristics, of the sole at the respective locations.

The direction of extension of the bottom surface, from the toe region to the heel region, defines a longitudinal (length) direction of the sole. The elongation direction of the one or more elongate grip members having the wave shape may be substantially in a lateral (width) direction of the sole, perpendicular to the longitudinal direction. The sole may be relatively more elastic in the lateral direction, e.g., more elastic than in the longitudinal direction. By extending in the lateral direction, the grip members may be particular suited to conforming to stretching of the sole in the lateral direction.

When a plurality of grip members are provided, the grip members may be spaced apart in the longitudinal direction of the sole. The spacing distance between each grip member may be substantially equal. The wave shapes of each grip member may be aligned in the longitudinal direction of the sole. For example, when the wave shapes of grip members have the same frequency, corresponding wave shape peaks of each grip member may be aligned along respective longitudinal axes of the sole. The equal spacing and/or the alignment of the wave shapes may ensure that the stretch characteristics of the sole can be substantially consistent over the area where they are located.

In addition to the one or more elongate grip members having the wave shape, the anti-slip means may comprise one or more other grip members having a different shape or configuration. For example, one or more additional grip members may be configured to partially or entirely surround one or more, or all, of the grip members having the wave shape. One such additional grip member may be an outer grip member and/or may be substantially U-shaped. The opening of the U-shape may be located toward the toe region of the foot portion. The toe region of the foot is generally the widest area of the foot, and stretching of the sole may be higher towards this region. By having the opening of the U-shape located toward the toe region, the ends of the U-shape may move apart to accommodate the stretching, without the U-shaped grip member being torn.

According to a second aspect, the present invention provides a compression stocking comprising:

a foot portion for covering at least portion of a wearer's foot, the foot portion including a toe region and a heel region and a sole extending between the toe region and heel region, the sole having a bottom surface for contacting a floor; and anti-slip means, the anti-slip means comprising a tread in the bottom surface of the sole and one or more grip members disposed on the bottom surface.

The combination of the tread and the one or more grip members can provide increased anti-slip function at the bottom surface of the sole. For example, the elongate grip members may partially or entirely overlay the tread and, when there is a plurality of spaced apart grip members, the tread may provide anti-slip function in spaces between the grip members.

One or more features of the first aspect of the invention may be combined with the second aspect of the invention and vice-versa. For example, in the second aspect, the one or more grip members may be elongate grip members having a wave shape as described with respect to the first aspect. However, alternative shapes for the grip members may be employed.

In the first or second aspects, the compression stocking may be formed at least partially of a fabric such as woven or knitted material and the tread may be formed through use of a particular construction of the fabric such as a particular weave or knit pattern. The fabric construction forming the tread may provide a rough, ribbed and/or bumpy region at the bottom surface of the sole. In one embodiment, weave forming the tread may comprise lower density stitching than weave forming other portions of the sole and/or other portions of the stocking.

The fabric construction forming the tread may provide the sole with a region of relatively high durability. The region may have greater thickness, strength and/or resistance to tearing. The fabric construction forming the tread may limit damage to the stocking caused through wear at the bottom surface.

In the first or second aspect, the anti-slip means may extend across part, or all, of the bottom surface of the sole. For example, the anti-slip means may extend across more than 50%, 60% 70%, 80%, or 90% of the bottom surface of the sole in the longitudinal direction of the sole. Likewise, the anti-slip means may extend across more than 50%, 60%, 70%, 80%, or 90% of the bottom surface of the sole in the lateral direction of the sole.

The compression stocking may comprise a toe opening. The toe opening may be located on the bottom surface of the sole, adjacent or at the toe region of the sole. The toe opening may be stretchable so that it can be stretched around one or more of the wearer's toes. The toe opening may be designed to be stretched around one or more toes only when needed to allow inspection of the toes while the stocking is worn. Alternatively, the toe opening may be designed to allow one or more toes to protrude from the stocking continually while the stocking is worn. The toe opening may be defined by a welt, e.g. an elastic welt.

To ensure that the anti-slip means provides anti-slip function close to the toe opening, at least a portion of the anti slip means, e.g., a portion of one or more of the grip members, may be located close to the toe opening. For example, at least a portion of the one or more grip members may be located at a distance of less than 3 cm, or less than 2 cm, or less than 1 cm, from the edge of the hole or from the edge of the welt.

The grip members may be provided by beading on the bottom surface of the sole. The grip members may comprise material having a relatively high coefficient of friction, in comparison to material forming the sole or foot portion, for example. The grip members may comprise a polymer, e.g. a silicon-based polymer such as polysiloxane/silicone, or natural rubber or other rubber-like material. The grip members may be applied to the sole as an ink. For example, a plastisol ink, e.g., an eco plastisol ink, may be applied to the sole via a screen printing technique or otherwise. The beading may therefore provide in one embodiment one or more relatively narrow, elongate, polymeric grip members, e.g., elongate silicone grip members having a width of less than 5 mm.

One or more of the grip members may be transparent or opaque. Accordingly, the grip members may be relatively inconspicuous on the bottom surface of the sole. This may ensure that the anti-slip means does not cause the compression stocking to look significantly different to ordinary compression stockings.

The compression stocking may further comprise a leg portion that extends from the foot portion up to the wearer's knee or thigh. The compression stocking may be a knee high stocking or a thigh high stocking.

The compression stocking may be a graduated compression stocking so that the pressure applied by the stocking to the wearer's leg decreases toward the top of the stocking.

According to a third aspect, the present invention provides a compression stocking comprising:

a foot portion for covering at least portion of a wearer's foot, the foot portion including a toe region and a heel region and a sole extending between the toe region and heel region, the sole having a bottom surface for contacting a floor, and anti-slip means, the anti-slip means comprising beading forming one or more grip members disposed on the bottom surface of the sole.

The one or more grip members of the third aspect may be configured in accordance with the one or more grip members of the first or second aspect. For example, as described above, the beading may provide one or more relatively narrow, elongate, polymeric grip members, e.g., elongate silicone grip members having a width of less than 5 mm. In any of the aspects, where the one or more grip members are formed of beading, the grip members may have a width of less than 5 mm, or less than 3 mm, or less than 2 mm, for example. The beading may be of material described with respect to the first and second aspects. For example, the beading may be silicone beading.

BRIEF DESCRIPTION OF THE DRAWINGS

Examples of the invention will now be described with reference to the accompanying drawings, in which.

DETAILED DESCRIPTION

Figure 1:
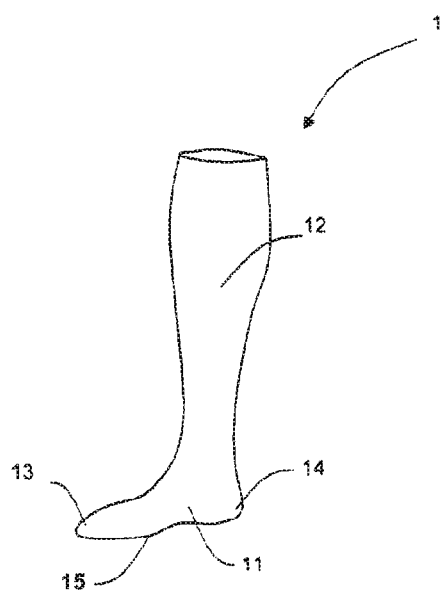
FIG. 1 shows a side view of a compression stocking according to a first embodiment of the present invention.

A compression stocking 1 according to a first embodiment of the present invention is shown in FIG. 1. The stocking 1 is a knee high stocking and comprises a foot portion 11 and a leg portion 12 extending upwardly from the foot portion 11. In use, i.e. when the stocking is worn by a wearer, the foot portion 11 is configured to cover the wearer's foot and the leg portion 12 is configured to cover the wearer's lower leg, up to their knee. The foot portion comprises a toe region 13 that, in use, locates over the toes of the wearer, and a heel region 14 that, in use, locates over the wearer's heel. The foot portion 11 further comprises a sole 15 that extends between the toe and heel regions 13, 14 that, in use, locates over the sole of the wearer's foot. The stocking 1 is designed to apply pressure to the wearer's leg and foot, particularly at the ankle, to reduce the wearer's risk of suffering an embolism, although compression stockings with other configurations and applications may be provided in alternative embodiments.

Figure 2:
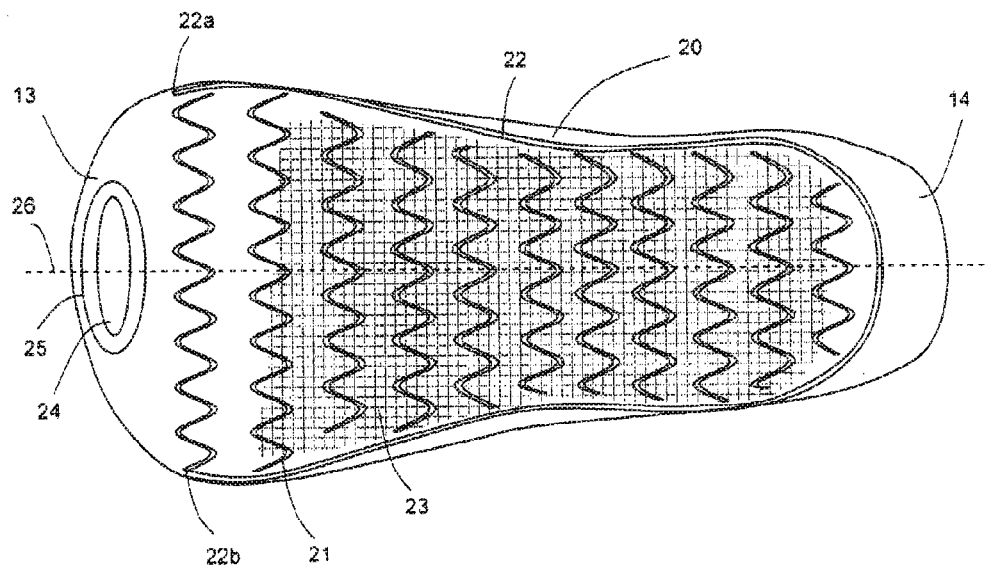
FIG. 2 shows a bottom view of the stocking of FIG. 1.

The sole 15 has a bottom surface 20 that, in use, can contact the floor or any other support surface that the wearer may stand on. The bottom surface 20 is best seen in FIG. 2, which shows a bottom view of the stocking of FIG. 1. An anti-slip means is provided at the sole, including a plurality of grip members 21, 22 and a tread 23.

The grip members 21, 22 include a plurality of elongate grip members 21 that are raised from the bottom surface 20 and each have a substantially sinusoidal wave shape. The elongation direction of each elongate grip member 21 is substantially in the lateral direction (width direction) of the sole 15, which direction is perpendicular to the longitudinal direction (length direction) of the sole 15, indicated by a hatched line 26 in FIG. 1. The elongate grip members 21 extend across most of the width of the bottom surface 20 of the sole 15. However, since the bottom surface 20 has a varying width along the length of the sole, the elongated grip members 21 also have different lengths. In general, the elongated grip members increase in length toward the toe region 13 of the sole 15, where the sole 15 is generally at its widest.

The elongate grip members 21 are spaced apart in the longitudinal direction 26 of the sole 15. The spacing in the longitudinal direction 26 between directly adjacent elongate grip members 21 is substantially equal. The oscillation pattern of each elongate grip member 21 is substantially the same, i.e., their wave shapes have oscillation frequencies and amplitudes that are substantially identical. Furthermore, the peaks and troughs of the wave shapes of each elongate grip member 21 are aligned in the longitudinal direction to corresponding peaks and troughs, where present, of the other grip members 21.

In this embodiment, the stocking 1 is a graduated compression stocking, formed mostly of a material comprising 25% spandex (elastane) and 75% nylon, and which can apply a compressive pressure of about 17 mm Hg or 18 mm Hg to the wearer's ankle when in a supine position. The stocking is preferably treated with an antimicrobial agent, such as Ultra-Fresh™. This treatment may provide a high antimicrobial performance to the stocking, killing greater than 99.999% of colony-forming units (CFU) of *staphylococcus aureus* (*s. aureus*) over a 30 wash period, for example. The grip members 21, 22 are clear and formed from silicone beading coated on the bottom surface 20. The silicone material forming the grip members 21, 22 is elastic and therefore stretchable. Stockings having different sizes can be provided as appropriate for the wearer. The sizing range can be designed to cover a large percentage of the population.

Figure 3A:
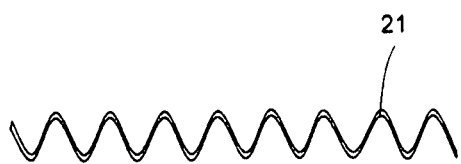
FIGS. 3a and 3b show a grip member of the stocking of FIGS. 1 and 2 before and after lateral stretching.
Figure 3B:

As the stocking 1 is put on, the material forming the stocking 1, including the sole 15, is designed to stretch. In this embodiment, stretching of the sole 15 occurs predominantly in the lateral direction of the sole 15. Due to the combination of the wave shape configuration of the elongate grip members 21, and the elastic nature of the material from which they are formed, the elongate grip members 21 can stretch in conformity with the sole 15. As a result, the elongate grip members 21 do not significantly alter the stretch characteristics of the sole 15. As the sole 15 stretches in the lateral direction, the wave shape of the elongate grip members 21 will tend toward a straighter line, as seen by a comparison of the grip members 21 in FIGS. 3*a* and 3*b*.

In addition to the elongate grip members 21, the anti-slip means includes a substantially U-shaped grip member 22 that partially surrounds all of the elongate grip members 21. Specifically, the U-shaped grip member 22 surrounds the elongate grip members 21 on all sides except at the toe region 13 end of the sole 15. In this embodiment, the U-shaped grip member 22 extends close to, but does not touch, the ends of the elongate grip members 21. The U-shaped grip member 22 can provide additional anti-slip properties at the lateral sides and heel end of the bottom surface 20. The toe region of the foot is generally wider than the heel region. Accordingly, stretching of the sole of the stocking 1 may be relatively higher towards the toe region 13. By having the opening of the U-shape located toward the toe region 13, the ends 22*a*, 22*b* of the U-shaped grip member 22 may move apart to accommodate the stretching, without the U-shaped grip member 22 being torn, for example.

In addition to the grip members 21, 22, the anti-slip means comprises a tread 23 formed in a portion of the bottom surface 20. The tread 23 in this embodiment is formed from a particular weave of the material forming the stocking at this region. The weave forming the tread in this embodiment is generally coarser than the weave forming other parts (e.g. directly adjacent parts) of the stocking. The weave is such as to form a plurality of ribs in the bottom surface 20. A number of the grip members 21 are provided overlying the tread.

The combination of the tread and the one or more grip members provides increased anti-slip function at the bottom surface 20. For example, the tread 23 provides anti-slip function in the spaces between some of the grip members 21.

The tread 23 also provides the sole 15 with a region of relatively high durability, with a greater thickness and resistance to tearing.

A toe opening 24 is provided on the bottom surface 20 of the sole adjacent the toe region 13 of the foot portion 11. The toe opening 24 is surrounded by an elastic welt 25. The welt 25 and toe opening 24 can be stretched open to surround one or more of the wearer's toes, when needed, to allow inspection of the toes while the stocking 1 is worn. To ensure that the anti-slip means provides anti-slip function close to the toe opening 25, a central portion of the elongate grip member 21 located closest to the toe opening 24 is located no more than 2 cm from the outer edge of the welt 25.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A compression stocking comprising:
   a foot portion for covering at least portion of a wearer's foot, the foot portion including a toe region and a heel region and a sole extending between the toe region and heel region, the sole having a woven or knitted bottom surface for contacting a floor; and
   anti-slip means provided at the bottom surface of the sole, the anti-slip means comprising:
   a plurality of polymeric elongate inner grip members, each inner grip member having a wave shape and each inner grip member overlaying at least a portion of the woven or knitted bottom surface; and
   a polymeric elongate outer grip member, the outer grip member comprising a continuous U-shaped polymeric strip of material that partially surrounds the plurality of inner grip members, wherein the opening of the U-shape is adjacent the toe region.

2. The compression stocking of claim 1, wherein the wave shape is a substantially sinusoidal shape.

3. The compression stocking of claim 1, wherein the wave shape is a substantially zigzag shape.

4. The compression stocking of claim 1, wherein the bottom surface of the sole extends between the toe region and heel region in a longitudinal direction of the sole and an elongation direction of the inner grip members having the wave shape are substantially in a lateral direction of the sole, perpendicular to a longitudinal direction.

5. The compression stocking of claim 4, wherein the inner grip members are spaced apart in the longitudinal direction of the sole.

6. The compression stocking claim 1, wherein the anti-slip means extends substantially the whole length of the sole between the toe region and heel region.

7. The compression stocking of claim 1 comprising a toe opening surrounded by a welt.

8. The compression stocking of claim 7, wherein at least a portion of one of the inner grip members is provided at a distance of no more than 2 cm from the welt.

9. The compression stocking claim 1, wherein the bottom surface comprises a tread.

10. The compression stocking of claim 9, wherein the tread provides the bottom surface of the sole with a rougher surface than surrounding surfaces of at least one of the foot portion and the bottom surface, and the anti-slip means overlays at least a portion of the woven or knitted tread.

11. The compression stocking of claim 1, wherein material of the stocking, forming at least the sole of the stocking, is antibacterially treated.

12. The compression stocking of claim 1, wherein the anti-slip means are elongate and have a width of less than 5 mm.

13. The compression stocking of claim 1, wherein the anti-slip means comprise silicone.

* * * * *